US007767714B2

(12) United States Patent
Shibahara (10) Patent No.: US 7,767,714 B2
(45) Date of Patent: Aug. 3, 2010

(54) METHOD OF PREVENTING INFECTIOUS DISEASES

(75) Inventor: Susumu Shibahara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1268 days.

(21) Appl. No.: 10/920,429

(22) Filed: Aug. 18, 2004

(65) Prior Publication Data

US 2005/0090511 A1    Apr. 28, 2005

Related U.S. Application Data

(63) Continuation-in-part of application No. PCT/JP03/01219, filed on Feb. 6, 2003.

(30) Foreign Application Priority Data

Feb. 18, 2002   (JP)   ............................. 2002-040845

(51) Int. Cl.
| | |
|---|---|
| A01N 37/12 | (2006.01) |
| A01N 37/44 | (2006.01) |
| A01N 37/06 | (2006.01) |
| A61K 31/195 | (2006.01) |
| A61K 31/225 | (2006.01) |
| C07C 321/00 | (2006.01) |
| C07C 323/00 | (2006.01) |
| C07C 381/00 | (2006.01) |

(52) U.S. Cl. ....................... 514/562; 514/561; 514/563; 514/547; 560/16

(58) Field of Classification Search .................. 514/562, 514/561, 563, 547; 560/16
See application file for complete search history.

(56) References Cited

FOREIGN PATENT DOCUMENTS

| EP | 0 764 442 A1 | 3/1997 |
|---|---|---|
| EP | 1 393 726 | 3/2004 |
| JP | 62-113785 | 5/1987 |
| JP | 2001-213774 | 8/2001 |
| WO | WO 98/30228 | 7/1998 |
| WO | WO 00/00158 | 1/2000 |
| WO | WO 01/56561 | 8/2001 |

OTHER PUBLICATIONS

Webster Ninth New Collegiate Dictionary. 2000. Definition of Prevention. p. 1.*
European Journal of Clinical Investigation, 2000. vol. 30, pp. 915-929.*
Webster Collegiate Ninth New Collegiate Dictionary. 2000, Defintion of Prevent, p. 1.*
Abstract: Database Biosis Biosciences Information Service, Philadelphia, PA, XP-002321580, Accession No. PREV200100193639, K. Nakachi et al, "Preventive effects of drinking green tea on cancer and cardiovascular disease: Epidemiological evidence for multiple targeting prevention", *Biofactors 2000*, 13 (1-4): 49-54, 2001.
Abstract: Database Biosis Biosciences Information Service, Philadelphia, PA, XP-002321581, Accession No. PREV200100511466, W.S. Joo et al, "Green tea prevents death of hippocampal CA1 neurons after global ischemia induced by four-vessel occlusion in rats", *31st Annual Meeting of the Society for Neuroscience*, San Diego, CA, 2001.
Abstract: Database FSTA International Food Information Service, Frankfurt-Main, Germany,XP-002321557, Accession No. 1999-00-H0266, "Effects of amino acids on green tea taste.",*Food Science*, China, 19 (3): 16-19, 1998.
Abstract: Database FSTA International Food Information Service, Frankfurt-Main, Germany,XP-002321558, Accession No. 84-3-04-H0846, K. Neumann et al, "Nitrogen compounds in tea (*Camellia sinensis*).", *Deutsche Lebensmittel-Rundschau*, 1983, 79 (5): 160, 1984.
*Nature*, vol. 166, Jul. 1, 1950 to Dec. 30, 1950, pp. 351-352.
N. Lightenstein et al, "Inhibition of the Growth of *Staphylococcus aureus* by Some Derivatives of Glutamic Acid", *The Journal of Biological Chemistry*, vol. 171, 1947, pp. 387-393.
Y. Oda et al, "Synthesis and Antibacterial Activities of Theanine-containing Oligopeptides", *Chem. Pharm. Bull.*, vol. 28, No. 12, 1980, pp. 3549-3554.
M. Asaka et al, "An Increase in Antibacterial Activity of Green Tea Infusion by Heat-Treatment", *Journal of Japanese Society for Food Science and Technology*, vol. 47, No. 9, 2000, pp. 708715.

* cited by examiner

*Primary Examiner*—Sreeni Padmanabhan
*Assistant Examiner*—Samira Jean-Louis
(74) *Attorney, Agent, or Firm*—Oblon, Spivak, McClelland, Maier & Neustadt, L.L.P.

(57) ABSTRACT

Effective preventive method for infectious diseases, an enhancing method of an infectious disease-preventive action of cystine and composition, food and feed effective for infectious diseases are provided.

A method of preventing infectious diseases wherein cystine and the like and theanine are administered in combination, a method of enhancing an infectious disease-preventive action of cystine and the like, which contains administering cystine and the like and theanine in combination, a pharmaceutical composition, food and feed wherein cystine and the like and theanine are combined.

59 Claims, 4 Drawing Sheets

METHOD OF PREVENTING INFECTIOUS DISEASES

CROSS REFERENCES TO RELATED APPLICATIONS

This application is a continuation-in-part of International Patent Application No. PCT/JP03/01219, filed on Feb. 6, 2003, and claims priority to Japanese Patent Application No. 40845/2002, filed on Feb. 18, 2002, both of which are incorporated herein by reference in their entireties.

BACKGROUND OF THE INVENTION

1. Field of the Invention

The present invention relates to a method of preventing infectious diseases, a method of enhancing an infectious disease-preventive action of cystine or a derivative thereof, a composition, food and feed, which are effective for the prevention of infectious diseases.

2. Discussion of the Background

Respiratory infectious viruses such as influenza virus, rhino virus, corona virus, parainfluenza virus, RS virus, adeno virus, reo virus and the like are causal viruses that grow in epithelial cells of from nasal cavity to pharynx, trachea, bronchus and to lung, and produce cold syndromes, namely, diseases often seen in daily lives with manifestations of cold symptoms. Most develop and recover from mild symptoms of rhinitis, pharyngitis and the like, but some develop severe complications such as pneumonia and the like, sometimes with fatal outcome, and these diseases require caution. When immunity decreases due to stress and the like and the living organism is not able to resist infection, a symptom appears. Currently, the treatment methods are generally symptomatic and non-prescription drugs such as cold remedy and the like, which contain antipyretic analgesics (e.g., acetaminophen and the like), drugs that suppress allergic symptoms (e.g., chlorpheniramine maleate and the like), antitussive and the like (e.g., methylephedrine hydrochloride and the like), are mostly taken. As the current situation stands, when the symptoms start to get rather worse, people go to hospital and receive the above-mentioned cold remedy, antimicrobial agents dealing with concurrent development of bacterial secondary infection and vitamins from doctors.

As a preventive prescription, preventive vaccination of inactivated vaccine against influenza prior to epidemic, which is the most important of these causal viruses, is given. There are many strains of influenza virus based on different surface antigens, which are susceptible to antigenic variation. Thus, inconsistency in the antigen structure between vaccine strain and epidemic strain is a significant problem. When a strain different from the vaccine inoculated based on prediction is in epidemic, the vaccination becomes ineffective. In addition, respiratory infectious viruses are known to include many kinds as described above, and each virus has many subspecies. Thus, a virus type selective preventive method may or may not be effective and, in some cases, the epidemic virus type (subspecies) may prove wrong.

Moreover, as a preventive method of infectious disease with respiratory infectious viruses, a gargle liquid of an iodine preparation has been used, but it is defective in that it has a distinctive bitter taste. While amantadine and rimantadine having an anti-influenza virus type A action have been used in the US for the prevention of infection (MMWR, 44, RR-3, 1995), they are associated with many restrictions on general prevalence from the aspects of the risk of emergence of resistant strain and possibility of side effects. Under the circumstances, preventive methods of infectious diseases with respiratory infectious viruses are not necessarily sufficient and there are problems yet to be solved.

On the other hand, there are several reports on the preventive and therapeutic agent for virus infectious diseases using sulfoamino acids such as cysteine and the like or a substance containing the same, such as a composition for prevention•treatment of influenza virus infection using a compound selected from glutathione, glutathione disulfide, ascorbate-2-phosphate and N-acetylcysteine (WO98/30228), a preventive agent of virus infectious diseases, which contains cysteine as an active ingredient (JP-A-2001-213774, WO01/56561), utilization of cystine, oxidized glutathione, S-alkylcysteine sulfoxide for the treatment of patients with human immunodeficient virus (EP0764442A1) and the like. However, it is undeniable that a more efficacious preventive agent can make a greater contribution to the medical field.

For the treatment•prevention of infectious diseases, administration of chemotherapeutic agents is general. However, new problems have been produced, such as emergence of bacteria that acquired resistance to pharmaceutical agents. In addition, the incidents of infection as a result of lower resistance to infection due to the use of immunosuppressants in more frequent occasions of used in recent years for the treatment of diseases have been increasing. Thus, appearance of an effective preventive agent has been desired.

Theanine is a γ ethylamide of glutamic acid and an amino acid contained at high levels in green tea. As regards its physiological action, there are many reports relating to the central action such as relaxing action, α wave induction action, suppression of caffeine rush and the like. As for antibacterial action of theanine, reports have been documented on the suppression of trichomonas growth by the addition of extremely high concentration of theanine in a vitro cultivation system (Nature, Vol. 166, 352, 1950), suppression of growth of *Staphylococcus aureus* (J. Biol. Chem. Vol. 171, 387, 1947), suppression of growth of *Staphylococcus aureus* and *Escherichia coli* (Chem. Pharm. Bull. Vol. 28, 3549-3554, 1980), and the like. On the other hand, a report has concluded that, what is mainly conducive to the antibacterial activity against *B. subtilis*, which is enhanced by heating the green tea extract, is not theanine but catechins (Journal of the Japanese Society for Food Science and Technology, Vol. 47, No. 9, 708-715, 2000). Moreover, there is no report on the effectiveness of theanine in the prevention of infectious diseases.

SUMMARY OF THE INVENTION

The present invention aims at providing a method of effectively preventing infectious diseases. In addition, the present invention aims at providing a method of enhancing an infectious disease-preventive action of cystine or a derivative thereof. The present invention further aims at providing a composition, food and feed effective for infectious diseases.

The present inventor has conducted intensive studies in an attempt to solve the above-mentioned problems and first found that theanine has an enhancing effect on the preventive action of cystine or a derivative thereof on infectious diseases, in other words, a combination of theanine and at least one kind selected from cystine and a derivative thereof (hereinafter to be also referred to as "cysteine and the like") exhibits high preventive effect against infectious diseases, which resulted in the completion of the present invention.

Accordingly, the present invention provides the following.

(1) An agent for preventing infectious diseases, which comprises theanine and at least one kind selected from cystine and a derivative thereof in combination.

(2) The preventive agent of the above-mentioned (1), wherein the infectious disease is a virus infectious disease.

(3) The preventive agent of the above-mentioned (1), wherein the infectious disease is a bacterial infectious disease.

(4) An enhancer of an infectious disease-preventive action of cystine or a derivative thereof, which comprises theanine.

(5) The enhancer of the above-mentioned (4), wherein the infectious disease is a virus infectious disease.

(6) The enhancer of the above-mentioned (4), wherein the infectious disease is a bacterial infectious disease.

(7) A commercial package comprising a concomitant agent comprising theanine and at least one kind selected from cystine and a derivative thereof in combination, and a written matter associated therewith, the written matter stating that the concomitant agent can or should be used for preventing infectious diseases.

(8) The commercial package of the above-mentioned (7), wherein the infectious disease is a virus infectious disease.

(9) The commercial package of the above-mentioned (7), wherein the infectious disease is a bacterial infectious disease.

(10) A commercial package comprising a concomitant agent comprising theanine, and a written matter associated therewith, the written matter stating that the concomitant agent can or should be used for enhancing an infectious disease-preventive action of cystine or a derivative thereof.

(11) The commercial package of the above-mentioned (10), wherein the infectious disease is a virus infectious disease.

(12) The commercial package of the above-mentioned (10), wherein the infectious disease is a bacterial infectious disease.

(13) A food or feed which comprises theanine and at least one kind selected from cystine and a derivative thereof in combination.

(14) The preventive agent of the above-mentioned (1), wherein at least one kind selected from cystine and a derivative thereof, and theanine are combined at a weight ratio of 100:1-1:100.

(15) The preventive agent of the above-mentioned (1), wherein a total dose of the at least one kind selected from cystine and a derivative thereof, and theanine is in the range of 100 μg/kg body weight/day-800 mg/kg body weight/day.

(16) The preventive agent of the above-mentioned (1), wherein a dose of the at least one kind selected from cystine and a derivative thereof is in the range of 1 μg/kg body weight/day-800 mg/kg body weight/day.

(17) The preventive agent of the above-mentioned (1), wherein a dose of theanine is in the range of 1 μg/kg body weight/day-800 mg/kg body weight/day.

(18) The commercial package of the above-mentioned (7), wherein at least one kind selected from cystine and a derivative thereof, and theanine are combined at a weight ratio of 100:1-1:100.

(19) The commercial package of the above-mentioned (7), wherein a total dose of at least one kind selected from cystine and a derivative thereof, and theanine is in the range of 100 μg/kg body weight/day-800 mg/kg body weight/day.

(20) The commercial package of the above-mentioned (7), wherein a dose of at least one kind selected from cystine and a derivative thereof is in the range of 1 μg/kg body weight/day-800 mg/kg body weight/day.

(21) The commercial package of the above-mentioned (7), wherein a dose of theanine is in the range of 1 μg/kg body weight/day-800 mg/kg body weight/day.

(22) A preventive method of infectious disease, which comprises administering theanine and at least one kind selected from cystine and a derivative thereof in combination.

(23) The method of the above-mentioned (22), wherein the infectious disease is a virus infectious disease.

(24) The method of the above-mentioned (22), wherein the infectious disease is a bacterial infectious disease.

(25) The method of the above-mentioned (22), wherein at least one kind selected from cystine and a derivative thereof, and theanine are combined at a weight ratio of 100:1-1:100.

(26) The method of the above-mentioned (22), wherein a total dose of at least one kind selected from cystine and a derivative thereof, and theanine is in the range of 100 μg/kg body weight/day-800 mg/kg body weight/day.

(27) The method of the above-mentioned (22), wherein a dose of at least one kind selected from cystine and a derivative thereof is in the range of 1 μg/kg body weight/day-800 mg/kg body weight/day.

(28) The method of the above-mentioned (22), wherein a dose of theanine is in the range of 1 μg/kg body weight/day-800 mg/kg body weight/day.

(29) A method of enhancing an infectious disease-preventive action of cystine or a derivative thereof, which comprises administering theanine and cystine or a derivative thereof in combination.

(30) The method of the above-mentioned (29), wherein the infectious disease is a virus infectious disease.

(31) The method of the above-mentioned (29), wherein the infectious disease is a bacterial infectious disease.

(32) Use of theanine and at least one kind selected from cystine and a derivative thereof for the production of an agent for preventing infectious diseases.

(33) The use of the above-mentioned (32), wherein the infectious disease is a virus infectious disease.

(34) The use of the above-mentioned (32), wherein the infectious disease is a bacterial infectious disease.

(35) The use of the above-mentioned (32), wherein at least one kind selected from cystine and a derivative thereof, and theanine are combined at a weight ratio of 100:1-1:100.

(36) The use of the above-mentioned (32), wherein a total dose of at least one kind selected from cystine and a derivative thereof, and theanine is in the range of 100 μg/kg body weight/day-800 mg/kg body weight/day.

(37) The use of the above-mentioned (32), wherein a dose of at least one kind selected from cystine and a derivative thereof is in the range of 1 μg/kg body weight/day-800 mg/kg body weight/day.

(38) The use of the above-mentioned (32), wherein a dose of theanine is in the range of 1 μg/kg body weight/day-800 mg/kg body weight/day.

(39) Use of theanine for the production of an enhancer of an infectious disease-preventive action of cystine or a derivative thereof.

(40) The use of the above-mentioned (39), wherein the infectious disease is a virus infectious disease.

(41) The use of the above-mentioned (39), wherein the infectious disease is a bacterial infectious disease.

(42) A pharmaceutical composition comprising theanine and at least one kind selected from cystine and a derivative thereof in combination.

(43) The pharmaceutical composition of the above-mentioned (42), which is used for preventing an infectious disease.

(44) The pharmaceutical composition of the above-mentioned (43), wherein the infectious disease is a virus infectious disease.

(45) The pharmaceutical composition of the above-mentioned (43), wherein the infectious disease is a bacterial infectious disease.

(46) A composition for enhancing an infectious disease-preventive action of cystine or a derivative thereof, which comprises theanine.

(47) The composition of the above-mentioned (46), wherein the infectious disease is a virus infectious disease.

(48) The composition of the above-mentioned (46), wherein the infectious disease is a bacterial infectious disease.

(49) The pharmaceutical composition of the above-mentioned (42), wherein at least one kind selected from cystine and a derivative thereof, and theanine are combined at a weight ratio of 100:1-1:100.

(50) The pharmaceutical composition of the above-mentioned (42), wherein a total dose of at least one kind selected from cystine and a derivative thereof, and theanine is in the range of 100 μg/kg body weight/day-800 mg/kg body weight/day.

(51) The pharmaceutical composition of the above-mentioned (42), wherein a dose of at least one kind selected from cystine and a derivative thereof is in the range of 1 μg/kg body weight/day-800 mg/kg body weight/day.

(52) The pharmaceutical composition of the above-mentioned (42), wherein a dose of theanine is in the range of 1 μg/kg body weight/day-800 mg/kg body weight/day.

(53) The food or feed of the above-mentioned (13), which is used for preventing an infectious disease.

(54) The food or feed of the above-mentioned (53), wherein the infectious disease is a virus infectious disease.

(55) The food or feed of the above-mentioned (53), wherein the infectious disease is a bacterial infectious disease.

(56) A food or feed for enhancing an infectious disease-preventive action of cystine or a derivative thereof, which comprises theanine.

(57) The food or feed of the above-mentioned (56), wherein the infectious disease is a virus infectious disease.

(58) The food or feed of the above-mentioned (56), wherein the infectious disease is a bacterial infectious disease.

(59) The food or feed of the above-mentioned (56), which is in the form selected from a beverage base powder, a beverage, and a confectionery.

(60) The food or feed of the above-mentioned (13), wherein at least one kind selected from cystine and a derivative thereof, and theanine are combined at a weight ratio of 100:1:-1:100.

(61) The food or feed of the above-mentioned (13), wherein a total amount of intake of at least one kind selected from cystine and a derivative thereof, and theanine is in the range of 100 μg/kg body weight/day-800 mg/kg body weight/day.

(62) The food or feed of the above-mentioned (13), wherein an amount of intake of at least one kind selected from cystine and a derivative thereof is in the range of 1 μg/kg body weight/day-800 mg/kg body weight/day.

(63) The food or feed of the above-mentioned (13), wherein an amount of intake of theanine is in the range of 1 μg/kg body weight/day-800 mg/kg body weight/day.

(64) The food or feed of the above-mentioned (13), which is in the form selected from a beverage base powder, a beverage, and a confectionery.

(65) A method of preventing an infectious disease, which comprises taking a food or feed comprising theanine and at least one kind selected from cystine and a derivative thereof in combination.

(66) The method of the above-mentioned (65), wherein the infectious disease is a virus infectious disease.

(67) The method of the above-mentioned (65), wherein the infectious disease is a bacterial infectious disease.

(68) The method of the above-mentioned (65), wherein the food or feed is in the form selected from a beverage base powder, a beverage, and a confectionery.

(69) The method of the above-mentioned (65), wherein at least one kind selected from cystine and a derivative thereof, and theanine are combined at a weight ratio of 100:1-1:100.

(70) The method of the above-mentioned (65), wherein a total amount of intake of at least one kind selected from cystine and a derivative thereof, and theanine is in the range of 100 μg/kg body weight/day-800 mg/kg body weight/day.

(71) The method of the above-mentioned (65), wherein an amount of intake of at least one kind selected from cystine and a derivative thereof is in the range of 1 μg/kg body weight/day-800 mg/kg body weight/day.

(72) The method of the above-mentioned (65), wherein an amount of intake of theanine is in the range of 1 μg/kg body weight/day-800 mg/kg body weight/day.

(73) A method of enhancing an infectious disease-preventive action of cystine or a derivative thereof, which comprises taking a food or feed comprising theanine and at least one kind selected from cystine and a derivative thereof in combination.

(74) The method of the above-mentioned (73), wherein the infectious disease is a virus infectious disease.

(75) The method of the above-mentioned (73), wherein the infectious disease is a bacterial infectious disease.

(76) The method of the above-mentioned (73), wherein the food or feed is in the form selected from a beverage base powder, a beverage, and a confectionery.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

The infectious diseases on which a method of preventing infectious diseases of the present invention (hereinafter sometimes to be simply referred to as a preventive method), a method of enhancing an infectious disease-preventive action of cystine or a derivative thereof of the present invention (hereinafter sometimes to be simply referred to as an enhancing method), a composition, food and feed of the present invention can be applied include, for example, virus infectious diseases and bacterial infectious diseases.

The virus infectious disease is not particularly limited and includes, for example, infectious diseases with respiratory infectious viruses (e.g., infectious diseases due to respiratory infectious viruses such as influenza virus, rhino virus, corona virus, parainfluenza virus, RS virus, adeno virus, reo virus and the like), herpes zoster caused by herpes virus, diarrhea caused by rotavirus, viral hepatitis, AIDS and the like. The present invention is particularly effective for infectious diseases with respiratory infectious viruses.

The bacterial infectious disease is not particularly limited and includes, for example, infectious diseases caused by *Bacillus cereus, Vibrio parahaemolyticus, Enterohemorrhagic Escherichia coli, Staphylococcus aureus*, MRSA, *Salmonella, Botulinus, Candida* and the like.

The cystine and cystine derivative to be used in the present invention are preferable of L-cystine.

The cystine derivative to be used in the present invention may be any as long as it is a compound derived from cysteine and has an infectious disease-preventive action. The cystine derivative includes cysteine, which is a monomer of cystine, and compounds derived from cysteine (cysteine derivatives). As the cystine derivative, for example, glutathione, glutathione disulfide (oxidized glutathione), glutathione alkyl ester (e.g., glutathione ethyl ester etc.), oxidized glutathione dialkyl ester (e.g., oxidized glutathione diethyl ester etc.), cysteine, cysteine alkyl ester (e.g., cysteine methyl ester, cysteine ethyl ester etc.), 3-[(carboxymethyl)thio]alanine, N-acylcysteine (e.g., N-acetylcysteine etc.), N-acylcysteine alkyl ester (e.g., N-acetylcysteine methyl ester, N-acetylcysteine ethyl ester etc.), N-acylcystine (e.g., N-acetylcystine etc.), N-acylcystine alkyl ester (e.g., N-acetylcystine methyl ester etc.), N,N'-diacylcystine (e.g., N,N'-diacetylcystine etc.), N,N'-diacylcystine dialkyl ester (e.g., N,N'-diacetylcystine dimethyl ester, N,N'-diacetylcystine diethyl ester etc.), S-alkylcysteine sulfoxide and the like can be mentioned.

The cystine and cystine derivative may take the form of a salt and the term "cystine and cystine derivative" in the present specification conceptually also encompasses salts.

Such salt is not particularly limited as long as it is pharmacologically acceptable, and, for example, salts with inorganic acid or organic acid can be mentioned. As the inorganic acid, for example, hydrochloric acid, hydrobromic acid, nitric acid, sulfuric acid, phosphoric acid and the like can be mentioned, and as the organic acid, formic acid, acetic acid, trifluoroacetic acid, propionic acid, lactic acid, tartaric acid, oxalic acid, fumaric acid, maleic acid, citric acid, malonic acid, methanesulfonic acid and the like can be mentioned. In addition, it can be a salt with a base. As the salt with a base, for example, alkali metal salts such as sodium salt, potassium salt and the like, alkaline earth metal salts such as calcium salt, magnesium salt and the like, and the like can be mentioned.

The theanine to be used in the present invention is preferably L-theanine.

The theanine may take the form of a salt and the term "theanine" in the present specification conceptually also encompasses salts.

Such salt is not particularly limited as long as it is pharmacologically acceptable, and, for example, salts with inorganic acid or organic acid can be mentioned. As the inorganic acid, for example, hydrochloric acid, hydrobromic acid, nitric acid, sulfuric acid, phosphoric acid and the like can be mentioned, and as the organic acid, formic acid, acetic acid, trifluoroacetic acid, propionic acid, lactic acid, tartaric acid, oxalic acid, fumaric acid, maleic acid, citric acid, malonic acid, methanesulfonic acid and the like can be mentioned. In addition, it can be a salt with a base. As the salt with a base, for example, alkali metal salts such as sodium salt, potassium salt and the like, alkaline earth metal salts such as calcium salt, magnesium salt and the like, and the like can be mentioned.

The preventive method, the enhancing method, the composition, the food and the feed of the present invention can be advantageously applied to human and animals other than human [e.g., mammals other than human (domestic animals such as pig, bovine, house, dog and the like), birds (domestic birds such as turkey, chicken and the like) and the like], and the like. Particularly, use thereof for economically supporting animals is an important use because it reduces economical loss of domestic birds and domestic animals, as well as prevents infection in human.

The preventive agent to be used for the preventive method of the present invention includes cystine and the like and theanine in combination (i.e., concomitant agent), and only need to be able to combine cystine and the like with theanine on administration. Accordingly, the preventive agent of the present invention may be a single preparation obtained by simultaneously formulating cystine and the like and theanine into a preparation or a combination of two kinds of preparations obtained by separately formulating cystine and the like and theanine into preparations, as long as cystine and the like with theanine can be combined on administration. The mode of administration is not particularly limited and, for example, (1) administration as a composition containing cystine and the like and theanine, namely, a single preparation, (2) simultaneous administration of 2 kinds of preparations obtained by separately formulating cystine and the like and theanine into preparations by the same administration route, (3) administration of 2 kinds of preparations obtained by separately formulating cystine and the like and theanine into preparations by the same administration route at staggered times (e.g., administration in the order of cystine and the like, then theanine, or in the reverse order), (4) simultaneous administration of 2 kinds of preparations obtained by separately formulating cystine and the like and theanine into preparations by different administration routes, (5) administration of 2 kinds of preparations obtained by separately formulating cystine and the like and theanine into preparations by different administration routes at staggered times (e.g., administration in the order of cystine and the like, then theanine, or in the reverse order) and the like can be mentioned.

In the case of administration at staggered times, it is necessary that the both be co-present in the body for the time necessary for theanine to enhance an infectious disease-preventive action of cystine and the like.

The enhancer to be used for the enhancing method of the present invention contains theanine and only need to be able to combine cystine and the like with theanine on administration. Accordingly, the enhancer of the present invention may, as long as it contains theanine, contain cystine and the like, or even if cystine and the like are not contained, cystine and the like can be separately administered as a concomitant agent. The mode of administration is not particularly limited and, for example, (1) administration of the enhancer of the present invention, which contains cystine and the like and theanine, (2) simultaneous administration of the enhancer of the present invention and cystine and the like by the same administration route, (3) administration of the enhancer of the present invention and cystine and the like by the same administration route at staggered times (e.g., administration in the order of cystine and the like, then the enhancer of the present invention, or in the reverse order), (4) simultaneous administration of the enhancer of the present invention and cystine and the like by different administration routes, (5) administration of the enhancer of the present invention and cystine and the like by different administration routes at staggered times (e.g., administration in the order of cystine and the like, then the enhancer of the present invention, or in the reverse order), and the like can be mentioned.

In the case of administration at staggered times, it is necessary that the both be co-present in the body, as in the case of the above-mentioned preventive agent.

In the present invention, the ratio of the combination of cystine and the like and theanine is, whether they are processed into a single preparation or separate preparations, generally in the range of 100:1-1:100, preferably in the range of 20:1-1:2, by weight ratio.

The total daily dose of cystine and the like and theanine is generally in the range of 100 µg/kg body weight-800 mg/kg body weight, preferably in the range of 500 µg/kg body weight-100 mg/kg body weight. However, the daily dose of cystine and the like is generally in the range of 1 µg/kg body weight-800 mg/kg body weight, preferably in the range of 100 µg/kg body weight-100 mg/kg body weight.

In the present invention, the daily dose of theanine is generally in the range of 1 µg/kg body weight-800 mg/kg body weight, preferably in the range of 20 µg/kg body weight-100 mg/kg body weight.

The above-mentioned daily dose can be administered once a day or in several portions a day. While the administration period is not particularly limited, it is generally in the range of 1-90 day(s), preferably in the range of 1-30 day(s).

The dosage form of the preventive agent and enhancer of the present invention is not particularly limited, and may be any of oral preparation and parenteral preparation. As the dosage form, for example, tablet, granule, powder, capsule, elixir, syrup, microcapsule or suspension and the like can be mentioned. The preventive agent and enhancer of the present invention can be orally or parenterally applied.

For parenteral administration, for example, a solution containing cystine and the like and theanine can be administered as a nasal spray or injection, and the like. The oral administration can be given any time, for example, before meals, after meals and between meals.

The preventive agent and enhancer of the present invention can contain carrier, excipient, binder, swelling agent, lubricant, sweetener, flavor, preservative, stabilizer, coating agent and the like, as necessary, and can be used in a unit dose requested for conventionally established practice of preparation. The amounts of cystine and the like and theanine in these compositions and preparations may be such doses that afford suitable dose in the specified range.

In the present invention, as specific components that can be contained in, for example, tablet, capsule and the like, for example, binders such as tragacanth, gum arabic, corn starch and gelatin; excipients such as micro-crystalline cellulose and crystalline cellulose; swelling agents such as corn starch, pregelatinized starch, alginic acid and dextrin; lubricants such as magnesium stearate; flowability improvers such as silicon dioxide microparticle; gloss agents such as glycerin fatty acid ester; sweeteners such as sucrose, lactose and aspartam; flavors such as peppermint, vanilla flavoring and cherry; and the like can be mentioned.

When the unit dosage form is a capsule, a liquid carrier such as fat can be further contained in the above-mentioned type of materials.

In addition, various other materials can be contained as coating agents or for changing the physical form of the unit dosage form. As the coating agent for tablet, for example, shellac, sugar or both of them can be mentioned. Syrup and elixir can contain, for example, sucrose as a sweetener, and methylparaben and propylparaben as preservatives, dye and cherry or orange flavor and the like. In addition, various vitamins and various amino acids may be contained.

When an enteric-coated preparation is produced, for example, an aqueous solution of hydroxyphenyl methyl cellulose is used as a pre-coating treating agent, and an aqueous solution of hydroxypropyl methyl cellulose phthalate and an aqueous solution of polyacetin are used as coating agents to give an enteric-coated preparation by a conventional method.

The present invention encompasses a commercial package comprising a concomitant agent comprising cystine and the like and theanine in combination, and a written matter associated therewith, the written matter stating that the concomitant agent can or should be used for preventing infectious diseases and a commercial package comprising a concomitant agent comprising theanine, and a written matter associated therewith, the written matter stating that the concomitant agent can or should be used for enhancing an infectious disease-preventive action of cystine or a derivative thereof.

The food and feed in the present invention comprise cystine and the like and theanine in combination, and may be any as long as cystine and the like and theanine can be combined when eating or drinking. Accordingly, the food or feed of the present invention may be a single food or feed containing cystine and the like and theanine, or a combination of two kinds of foods or feeds, wherein one of them contains cystine and the like and the other contains theanine, as long as cystine and the like and theanine can be combined when taking the food or feed. The mode of taking may follow the administration mode in the above-mentioned preventive method.

When the food or feed of the present invention is used for enhancing the infectious disease-preventive action of cystine and the like, it only needs to contain theanine, and may be any as long as cystine and the like and theanine can be combined when taking the food or feed. Therefore, as long as it contains theanine, it may contain cystine and the like, or even if it does not contain cystine and the like, cystine and the like can be concurrently and separately taken. The mode of taking may follow the administration mode in the above-mentioned enhancing method.

The amount of cystine and the like and theanine contained in the food and feed is not particularly limited, but preferably the amount drunk or eaten a day is in the same range as the above-mentioned dose of the preventive agent and the enhancer of the present invention.

In the food and feed of the present invention, the weight ratio of a combination of cystine and the like with theanine is generally in the range of 100:1-1:100, preferably 20:1-1:2, whether the both are contained in a single food or feed or in a separate food or feed.

The total amount of intake of cystine and the like and theanine is generally in the range of 100 µg/kg body weight/day-800 mg/kg body weight/day, preferably 500 µg/kg body weight/day-100 mg/kg body weight/day. However, an amount of intake of cystine and the like is generally in the range of 1 µg/kg body weight/day-800 mg/kg body weight/day, preferably 100 µg/kg body weight-100 mg/kg body weight/day.

In the present invention, an amount of intake of theanine is generally in the range of 1 µg/kg body weight/day-800 mg/kg body weight/day, preferably 20 µg/kg body weight-100 mg/kg body weight/day.

The above-mentioned daily amount can be taken once a day or in several portions a day. While the period of intake is not particularly limited, it is generally in the range of 1-90 day(s), preferably in the range of 1-30 day(s).

While the form of the food is not particularly limited, for example, one wherein cystine and the like and theanine are added to drinks and food such as beverage base powder such as milk powder and the like, beverage, confectionery, chocolate, candy, chewing gum, tablet confectionery, bakery products, snack, marine processed food, processed food of meat from domestic animals, retort food, frozen food, instant noodle, soup, yogurt, health food and the like, and the like can be mentioned.

The "food" in the present invention means food in general, which includes general food including what is called health food, as well as food for specified health use and food with nutrient function claims, specified in the Food with health claims system by the Japanese Ministry of Health, Labour and Welfare, further including dietary supplements. In addition, the preventive agent and enhancer of the present invention can be applied to feed use, and can be administered to domestic birds, domestic animals and the like by addition to general feed.

Other features of the invention will become apparent in the course of the following descriptions of exemplary embodiments which are given for illustration of the invention and are not intended to be limiting thereof.

EXAMPLES

Example 1

4-week-old BALB/c female mice in the growth period were preliminarily raised on a solid feed (CRF-1 solid feed, Charles River Japan, inc.) for one week, then preliminarily raised on a powder feed (CRF-1 powder feed, Charles River Japan, inc.) for one week, and when they reached 6 weeks of age, the feed was changed to a feed containing 20 wt % of casein as a protein source (basic feed: composition: α-corn starch 68.3 wt %, casein 20 wt %, mineral mixture 3.5 wt %, vitamin mixture 1 wt %, cellulose powder 2 wt %, corn-oil 5 wt %, choline bitartrate 0.2 wt %), the same feed supplemented with 0.5 wt % of L-cystine as an amino acid, the same feed supplemented with 0.2 wt % of L-theanine as an amino acid, and the same feed supplemented with 0.5 wt % of L-cystine and 0.2 wt % of L-theanine as amino acids (the present invention), and further raised for 2 weeks. Those continuously raised on the basic feed were used as a control group. Ten mice were used for the test for each group.

Figure 1:
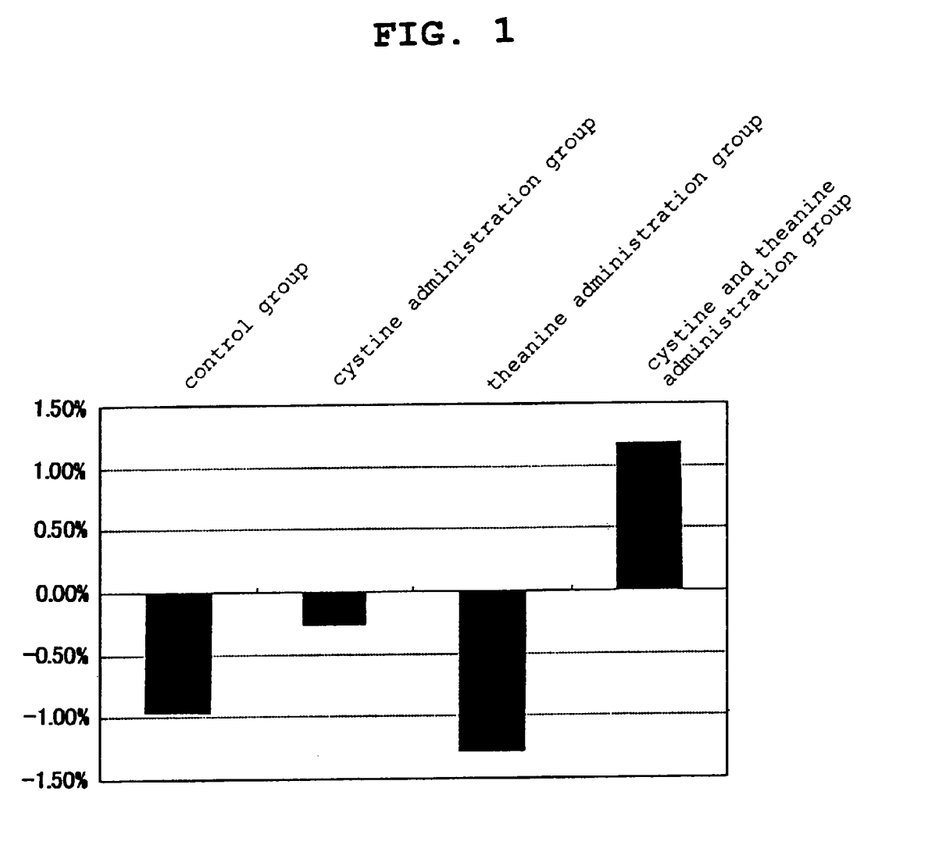
FIG. 1 shows body weight change rates of mouse at day 5 of influenza virus infection in Example 1.

At two weeks of the amino acid addition feed administration, $10^5$ PFU influenza virus A/Aichi/2/68 (H3N2) was nasally inoculated, the body weight of the mice was measured immediately before virus inoculation and day 5 of infection. The results are shown in FIG. 1. While the control group showed decrease in the body weight in 5 days of infection, the body weight decrease rate of the L-cystine addition group was suppressed somewhat. In contrast, L-cystine and L-theanine addition group conversely showed a body weight increase. It was found that the body weight decrease as a disorder effect induced by influenza virus infection was suppressed and that the effect thereof was stronger than exclusive administration of L-cystine.

The L-theanine addition group showed a body weight decrease of the same level as that of the control group and L-theanine alone did not show an effect. Thus, it was clarified that a concurrent use of L-theanine enhanced the action of L-cystine.

The daily intake of L-cystine and L-theanine by mouse in Example 1 is 0.5 wt % and 0.2 wt %, respectively, of the feed. Since the protein (casein) amount of the standard feed is 20 wt %, the figures correspond to 2.5 wt % and 1 wt % thereof. Based on this ratio and from the recommended protein allowances of Japanese (Recommended Dietary Allowances for the Japanese 6th Revision, the Japanese Ministry of Health, Labour and Welfare) of 55-85 g/day, the dose for human is calculated to be 1.375-2.125 g/day for L-cystine and 0.55-0.85 g/day for L-theanine, and the effect has been confirmed with these amounts.

Example 2

5-week-old BALB/c female mice in the growth period were preliminarily raised on a solid feed (CRF-1 solid feed, Charles River Japan, inc.) for one week, then a feed containing 20 wt % of casein as a protein source was given to control group and the same feed supplemented with 0.8 wt % of L-cystine and 0.2 wt % of L-theanine as amino acids (the present invention) was given to test group while raising for 2 weeks.

Figure 2:
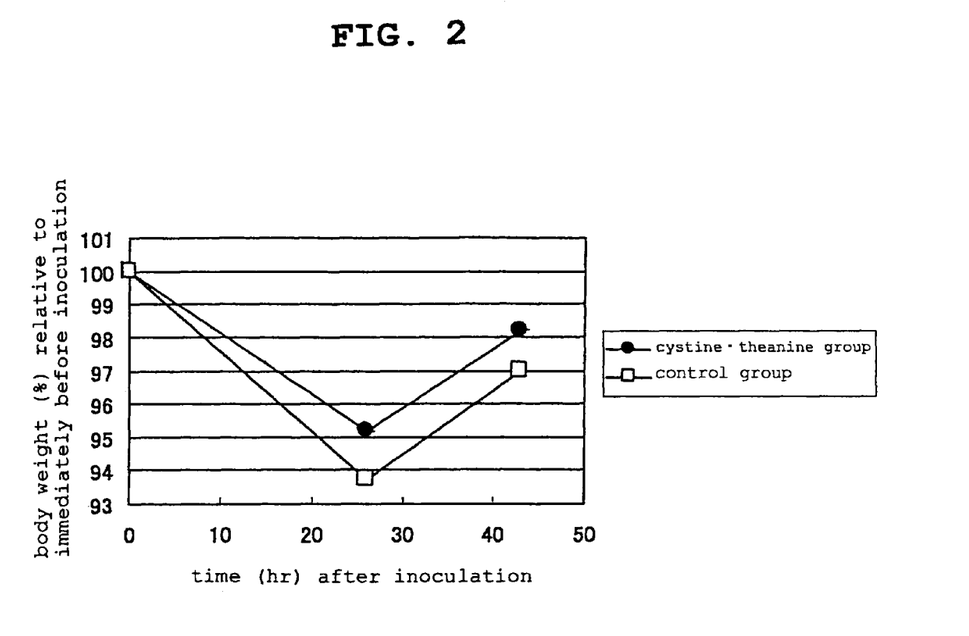
FIG. 2 shows body weight change of mouse after inoculation of bacterial endotoxin lipopolysaccharide derived from *Escherichia coli* serotype 055:B5 in Example 2.

At two weeks of the amino acid addition feed administration, *Escherichia coli* serotype O55:B5 derived lipopolysaccharide (Sigma) was intraperitoneally inoculated as bacterial toxin at 40 μg for each mouse, and the body weight was measured immediately before inoculation, 26 hr later and 43 hr later. The results are shown in FIG. 2. As compared to the control group, L-cystine and L-theanine administration group clearly showed lowering body weight decrease rate both at 26 hr later and 43 hr later, thereby also showing effectiveness in the suppression of body weight decrease disorder due to bacterial endotoxin.

The daily intake of L-cystine and L-theanine by mouse in Example 2 is 0.8 wt % and 0.2 wt %, respectively, of the feed. Since the protein (casein) amount of the standard feed is 20 wt %, the figures correspond to 4 wt % and 1 wt % thereof. Based on this ratio and from the recommended protein allowances of Japanese (Recommended Dietary Allowances for the Japanese 6th Revision, the Japanese Ministry of Health, Labour and Welfare) of 55-85 g/day, the dose for human is calculated to be 2.2-3.4 g/day for L-cystine and 0.55-0.85 g/day for L-theanine, and the effect has been confirmed with these amounts.

Example 3

4-week-old BALB/c female mice in the growth period were preliminarily raised on a solid feed (CRF-1 solid feed, Charles River Japan, inc.) for 3 days, then a feed containing 20 wt % of casein as a protein source was given to control group and the same feed supplemented with 0.8 wt % of L-cystine and 0.2 wt % of L-theanine as amino acids (the present invention) was given to test group A, and the same feed supplemented with 0.8 wt % of N-acetylcysteine and 0.2 wt % of L-theanine as amino acids (the present invention) was given to test group B while raising for 11 days.

Figure 3:
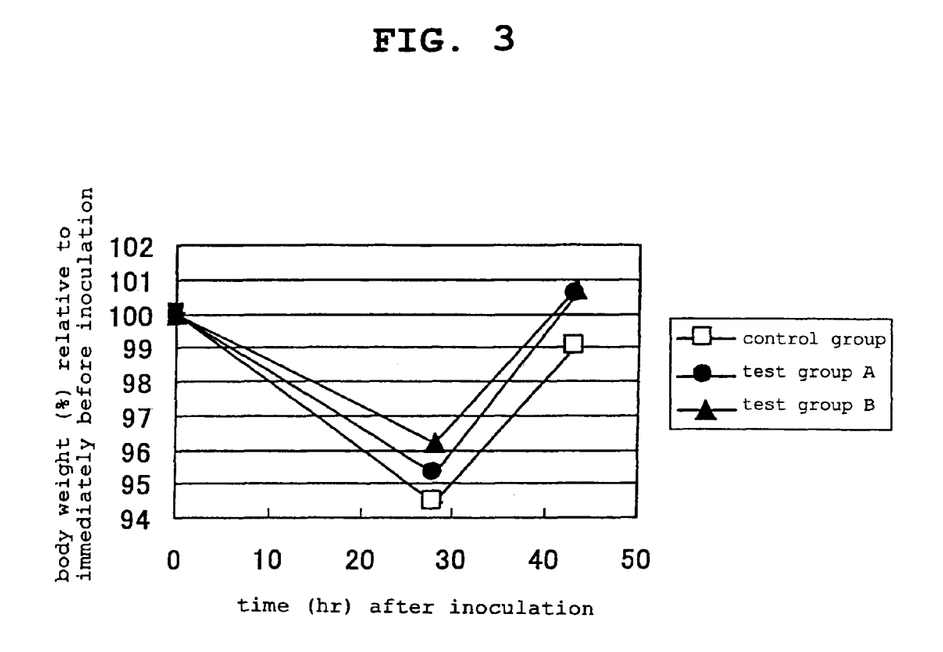
FIG. 3 shows body weight change of mouse after inoculation of bacterial endotoxin lipopolysaccharide derived from *Escherichia coli* serotype 055:B5 in Example 3.

At 11 days of the amino acid addition feed administration, *Escherichia coli* serotype O55:B5 derived lipopolysaccharide (Sigma) was intraperitoneally inoculated as bacterial toxin at 40 μg for each mouse, and the body weight was measured immediately before inoculation, 28 hr later and 43 hr later. The results are shown in FIG. 3. As compared to the control group, test group A and test group B clearly showed suppression of body weight decrease both at 28 hr later and 43 hr later, thereby also showing effectiveness in the suppression of body weight decrease disorder due to bacterial endotoxin.

Example 4

(Cystine, Theanine-Containing Preparation)

L-cystine 2,625 g, L-theanine 1,050 g, dextrin 1,710 g and aspartam 15 g were mixed, crystalline cellulose 1,500 g and 70% ethanol (30% by weight ratio) were added, kneaded and extrusion-granulated. The obtained granule was dried to moisture content of not more than 1.6%, sieved to give 16 mesh pass particles. Thereto were added silicon dioxide microparticles 37.5 g, glycerin fatty acid ester 487.5 g and vanilla flavoring 75 g and mixed. The obtained mixture was tableted under the conditions of 11 mmϕ, 500 mg, tableting pressure 2.0 ton, revolution 20 rpm, hardness average 10 kg. By the above operation, diameter 11 mmϕ tablets containing 175 mg of L-cystine and 70 mg of L-theanine per tablet were produced.

(Placebo Preparation)

Glycine 3,675 g, dextrin 1,725 g and glycerin fatty acid ester 375 g were mixed, crystalline cellulose 1,500 g and 70% ethanol (22% by weight ratio) were added, kneaded and extrusion-granulated. The obtained granule was dried to moisture content of 2.28%, sieved to give 16 mesh pass particles. Thereto were added silicon dioxide microparticles 150 g and vanilla flavoring 75 g and mixed. The obtained mixture was tableted under the conditions of 11 mmϕ, 500 mg, tableting pressure 2.2 ton, revolution 20 rpm, hardness average 10 kg. By the above operation, diameter 11 mmϕ tablets containing 245 mg of glycine per tablet were produced.

Example 5

176 Healthy adult males were allocated into two groups of a cystine•theanine tablet intake group (88 males) (test group) and a glycine tablet intake group (85 males) (placebo group) by random allocation, and subjected to a double blind intergroup comparison study. The average age was 39.8 for the test group and 39.6 for the placebo group. The test lasted for 5 weeks, during which the tablets described in the above-mentioned Example 4 were taken twice a day after breakfast and supper, two tablets per administration, and observation of oneself relating to cold symptoms was recorded every day before going to bed. The observation items of the subjective and objective symptoms were 1. cold symptoms: runny nose, stuffy nose, sneeze, throat pain, cough, phlegm, chill, fever (body temperature), headache, joint pain, skin pain, general malaise, 2. symptoms accompanying cold: nausea, emesis, abdominal pain, diarrhea, hypophagia, chest pain, eruption, 3. other subjective and objective symptoms and for each item, three levels of "no symptom" as −, "rather symptomatic" as ±, and "symptomatic" as + were recorded. The intake rate was 88% for the test group and 91% for the placebo group.

The test records were scored, wherein "no symptom" (−) was scored 0, "rather symptomatic" (±) was scored 1 and "symptomatic" (+) was scored 2 for each symptom for each day, the symptoms were classified into four categories of nose, throat, chill and fever, and pain sensation, and when not less than 3 items of the total scores of the following symptom classification items I-IV were met, the symptom was defined as a "cold".

I. With nose symptoms of runny nose, stuffy nose and sneeze as objects, the total score of these three symptoms is not less than 3, II. with throat symptoms of throat pain, cough and phlegm as objects, the total score of these three symptoms is not less than 3, III. with chill and fever as objects, the total score of these two symptoms is not less than 2, IV. with pain sensation symptoms of headache, joint pain and skin pain as objects, the total score of these three symptoms is not less than 3.

Figure 4:
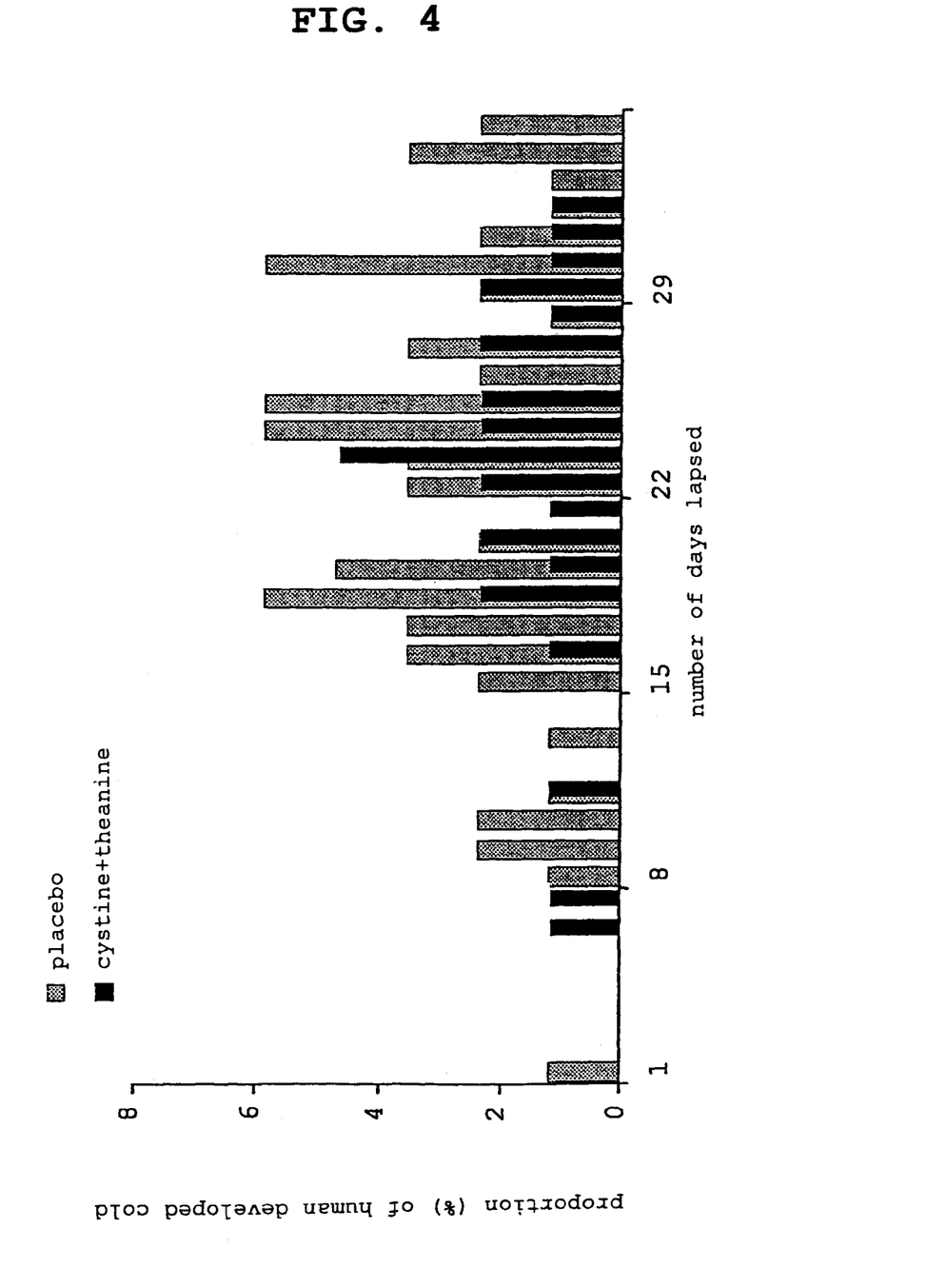
FIG. 4 shows shift in the "cold" onset rates for each day passed in Example 4.

The frequency of the onset of the cold is shown in FIG. 4, wherein almost on every day of progress, the test group showed lower onset as compared to the placebo group, and intergroup comparison based on the analysis of variance with the lapse of day by a cumulative $\chi^2$ test revealed a 5% significant (p=0.0160) in the intergroup difference throughout the entire days lapsed, whereby the cystine•theanine tablet intake group was confirmed to show lower incidence of the onset of cold than the placebo group.

INDUSTRIAL APPLICABILITY

The preventive method of infectious diseases, the enhancing method of an infectious disease-preventive action of cystine and the like, and the composition, the food and the feed of the present invention have a high preventive effect on infectious diseases due to the combination of cystine and the like with theanine.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of enhancing an infectious disease-treating action of cystine or a derivative of cystine, which comprises administering, to a subject in need thereof, an effective amount of theanine or a salt thereof and cystine or a salt thereof or a derivative of cystine in combination,
wherein said derivative of cystine is selected from the group consisting of glutathione, glutathione disulfide, a glutathione alkyl ester, an oxidized glutathione dialkyl ester, cysteine, a cysteine alkyl ester, 3-[(carboxymethyl)thio]alanine, an N-acylcysteine, an N-acylcysteine alkyl ester, an N-acylcystine, an N-acylcystine alkyl ester, an N,N'-diacylcystine, an N,N'-diacylcystine dialkyl ester, S-alkylcysteine sulfoxide, and salts thereof.

2. The method of claim 1, wherein the infectious disease is a virus infectious disease.

3. The method of claim 1, wherein the infectious disease is a bacterial infectious disease.

4. A method of enhancing an infectious disease-treating action of cystine or a derivative of cystine, which comprises taking a food or feed comprising theanine or a salt thereof and at least one member selected from the group consisting of cystine, a salt of cystine, and a derivative of cystine in combination,
wherein said derivative of cystine is selected from the group consisting of glutathione, glutathione disulfide, a glutathione alkyl ester, an oxidized glutathione dialkyl ester, cysteine, a cysteine alkyl ester, 3-[(carboxymethyl)thio]alanine, an N-acylcysteine, an N-acylcysteine alkyl ester, an N-acylcystine, an N-acylcystine alkyl ester, an N,N'-diacylcystine, an N,N'-diacylcystine dialkyl ester, S-alkylcysteine sulfoxide, and salts thereof.

5. The method of claim 4, wherein the infectious disease is a virus infectious disease.

6. The method of claim 4, wherein the infectious disease is a bacterial infectious disease.

7. The method of claim 4, wherein the food or feed is in the form selected from a beverage base powder, a beverage, and a confectionery.

8. The method of claim 1, wherein said derivative of cystine is N-acetylcysteine.

9. The method of claim 1, comprising administering theanine or a salt thereof in combination with cystine or a salt thereof or N-acetylcysteine or a salt thereof.

10. The method of claim 4, wherein said derivative of cystine is N-acetylcysteine.

11. The method of claim 4, wherein said food or feed comprises theanine or a salt thereof in combination with cystine or a salt thereof or N-acetylcysteine or a salt thereof.

12. The method of claim 1, wherein the total daily dose of said cystine or derivative of cystine and said theanine is in the range of 100 μg/kg body weight to 800 mg/kg body weight.

13. The method of claim 1, wherein the total daily dose of said cystine or derivative of cystine and said theanine is in the range of 500 μg/kg body weight to 100 mg/kg body weight.

14. The method of claim 1, wherein the daily dose of said cystine or said derivative of cystine is in the range of 1 μg/kg body weight to 800 mg/kg body weight.

15. The method of claim 1, wherein the daily dose of said cystine or said derivative of cystine is in the range of 100 μg/kg body weight to 100 mg/kg body weight.

16. The method of claim 1, wherein the daily dose of said theanine is in the range of 1 μg/kg body weight to 800 mg/kg body weight.

17. The method of claim 1, wherein the daily dose of said theanine is in the range of 20 μg/kg body weight to 100 mg/kg body weight.

18. The method of claim 4, wherein the total daily dose of said cystine or derivative of cystine and said theanine is in the range of 100 μg/kg body weight to 800 mg/kg body weight.

19. The method of claim 4, wherein the total daily dose of said cystine or derivative of cystine and said theanine is in the range of 500 μg/kg body weight to 100 mg/kg body weight.

20. The method of claim 4, wherein the daily dose of said cystine or said derivative of cystine is in the range of 1 μg/kg body weight to 800 mg/kg body weight.

21. The method of claim 4, wherein the daily dose of said cystine or said derivative of cystine is in the range of 100 μg/kg body weight to 100 mg/kg body weight.

22. The method of claim 4, wherein the daily dose of said theanine is in the range of 1 μg/kg body weight to 800 mg/kg body weight.

23. The method of claim 4, wherein the daily dose of said theanine is in the range of 20 μg/kg body weight to 100 mg/kg body weight.

24. A method of reducing the risk of contracting a viral or bacterial infection, which comprises administering, to a subject in need thereof, an effective amount of theanine or a salt thereof and cystine or a salt thereof or a derivative of cystine in combination, wherein said derivative of cystine is selected from the group consisting of glutathione, glutathione disulfide, a glutathione alkyl ester, an oxidized glutathione dialkyl ester, cysteine, a cysteine alkyl ester, 3-[(carboxymethyl)thio]alanine, an N-acylcysteine, an N-acylcysteine alkyl ester, an N-acylcystine, an N-acylcystine alkyl ester, an N,N'-diacylcystine, an N,N'-diacylcystine dialkyl ester, S-alkylcysteine sulfoxide, and salts thereof.

25. A method of reducing the severity of a viral or bacterial infection, which comprises administering, to a subject in need thereof, an effective amount of theanine or a salt thereof and cystine or a salt thereof or a derivative of cystine in combination, wherein said derivative of cystine is selected from the group consisting of glutathione, glutathione disulfide, a glutathione alkyl ester, an oxidized glutathione dialkyl ester, cysteine, a cysteine alkyl ester, 3-[(carboxymethyl)thio]alanine, an N-acylcysteine, an N-acylcysteine alkyl ester, an N-acylcystine, an N-acylcystine alkyl ester, an N,N'-diacylcystine, an N,N'-diacylcystine dialkyl ester, S-alkylcysteine sulfoxide, and salts thereof.

26. A method of reducing the risk of contracting a viral or bacterial infection, which comprises taking a food or feed comprising theanine or a salt thereof and at least one member selected from the group consisting of cystine, a salt of cystine, and a derivative of cystine in combination, wherein said derivative of cystine is selected from the group consisting of glutathione, glutathione disulfide, a glutathione alkyl ester, an oxidized glutathione dialkyl ester, cysteine, a cysteine alkyl ester, 3-[(carboxymethyl)thio]alanine, an N-acylcysteine, an N-acylcysteine alkyl ester, an N-acylcystine, an N-acylcystine alkyl ester, an N,N'-diacylcystine, an N,N'-diacylcystine dialkyl ester, S-alkylcysteine sulfoxide, and salts thereof.

27. A method of reducing the severity of a viral or bacterial infection, which comprises taking a food or feed comprising theanine or a salt thereof and at least one member selected from the group consisting of cystine, a salt of cystine, and a derivative of cystine in combination, wherein said derivative of cystine is selected from the group consisting of glutathione, glutathione disulfide, a glutathione alkyl ester, an oxidized glutathione dialkyl ester, cysteine, a cysteine alkyl ester, 3-[(carboxymethyl)thio]alanine, an N-acylcysteine, an N-acylcysteine alkyl ester, an N-acylcystine, an N-acylcystine alkyl ester, an N,N'-diacylcystine, an N,N'-diacylcystine dialkyl ester, S-alkylcysteine sulfoxide, and salts thereof.

28. The method of claim 1, wherein said infectious disease is an influenza virus infection.

29. The method of claim 1, wherein said infectious disease is an *E. coli* infection.

30. The method of claim 4, wherein said infectious disease is an influenza virus infection.

31. The method of claim 4, wherein said infectious disease is an *E. coli* infection.

32. The method of claim 24, wherein said viral or bacterial infection is an influenza virus infection.

33. The method of claim 24, wherein said viral or bacterial infection is an *E. coli* infection.

34. The method of claim 25, wherein said viral or bacterial infection is an influenza virus infection.

35. The method of claim 25, wherein said viral or bacterial infection is an *E. coli* infection.

36. The method of claim 26, wherein said viral or bacterial infection is an influenza virus infection.

37. The method of claim 26, wherein said viral or bacterial infection is an *E. coli* infection.

38. The method of claim 27, wherein said viral or bacterial infection is an influenza virus infection.

39. The method of claim 27, wherein said viral or bacterial infection is an *E. coli* infection.

40. The method of claim 24, comprising administering theanine or a salt thereof in combination with cystine or a salt thereof or N-acetylcysteine or a salt thereof.

41. The method of claim 25, comprising administering theanine or a salt thereof in combination with cystine or a salt thereof or N-acetylcysteine or a salt thereof.

42. The method of claim 26, comprising administering theanine or a salt thereof in combination with cystine or a salt thereof or N-acetylcysteine or a salt thereof.

43. The method of claim 27, comprising administering theanine or a salt thereof in combination with cystine or a salt thereof or N-acetylcysteine or a salt thereof 44. The method of claim 40, wherein the total daily dose of said cystine or N-acetylcysteine and said theanine is in the range of 100 µg/kg body weight to 800 mg/kg body weight.

45. The method of claim 41, wherein the total daily dose of said cystine or N-acetylcysteine and said theanine is in the range of 100 µg/kg body weight to 800 mg/kg body weight.

46. The method of claim 42, wherein the total daily dose of said cystine or N-acetylcysteine and said theanine is in the range of 100 µg/kg body weight to 800 mg/kg body weight.

47. The method of claim 43, wherein the total daily dose of said cystine or N-acetylcysteine and said theanine is in the range of 100 µg/kg body weight to 800 mg/kg body weight.

48. The method of claim 40, wherein the daily dose of said cystine or N-acetylcysteine is in the range of 100 µg/kg body weight to 100 mg/kg body weight.

49. The method of claim 41, wherein the daily dose of said cystine or N-acetylcysteine is in the range of 100 µg/kg body weight to 100 mg/kg body weight.

50. The method of claim 42, wherein the daily dose of said cystine or N-acetylcysteine is in the range of 100 µg/kg body weight to 100 mg/kg body weight.

51. The method of claim 43, wherein the daily dose of said cystine or N-acetylcysteine is in the range of 100 µg/kg body weight to 100 mg/kg body weight.

52. The method of claim 40, wherein the daily dose of said theanine is in the range of 20 µg/kg body weight to 100 mg/kg body weight.

53. The method of claim 41, wherein the daily dose of said theanine is in the range of 20 µg/kg body weight to 100 mg/kg body weight.

54. The method of claim 42, wherein the daily dose of said theanine is in the range of 20 µg/kg body weight to 100 mg/kg body weight.

55. The method of claim 43, wherein the daily dose of said theanine is in the range of 20 µg/kg body weight to 100 mg/kg body weight.

56. The method of claim 40, wherein the daily dose of said cystine or N-acetylcysteine is in the range of 100 µg/kg body weight to 100 mg/kg body weight, and the daily dose of said theanine is in the range of 20 µg/kg body weight to 100 mg/kg body weight.

57. The method of claim 41, wherein the daily dose of said cystine or N-acetylcysteine is in the range of 100 µg/kg body weight to 100 mg/kg body weight, and the daily dose of said theanine is in the range of 20 µg/kg body weight to 100 mg/kg body weight.

58. The method of claim 42, wherein the daily dose of said cystine or N-acetylcysteine is in the range of 100 µg/kg body weight to 100 mg/kg body weight, and the daily dose of said theanine is in the range of 20 µg/kg body weight to 100 mg/kg body weight.

59. The method of claim 43, wherein the daily dose of said cystine or N-acetylcysteine is in the range of 100 µg/kg body weight to 100 mg/kg body weight, and the daily dose of said theanine is in the range of 20 µg/kg body weight to 100 mg/kg body weight.

\* \* \* \* \*